(12) United States Patent
Grodzins

(10) Patent No.: US 7,302,034 B2
(45) Date of Patent: Nov. 27, 2007

(54) ANALYSIS OF ELEMENTAL COMPOSITION AND THICKNESS IN MULTILAYERED MATERIALS

(75) Inventor: Lee Grodzins, Lexington, MA (US)

(73) Assignee: ThermoNITON Analyzers LLC, Billerica, MA (US)

( * ) Notice: Subject to any disclaimer, the term of this patent is extended or adjusted under 35 U.S.C. 154(b) by 0 days.

(21) Appl. No.: 11/538,652

(22) Filed: Oct. 4, 2006

(65) Prior Publication Data

US 2007/0092060 A1     Apr. 26, 2007

Related U.S. Application Data

(60) Provisional application No. 60/723,384, filed on Oct. 4, 2005.

(51) Int. Cl.
*G01B 15/02*     (2006.01)
(52) U.S. Cl. ....................................................... 378/50
(58) Field of Classification Search ............ 378/44–50
See application file for complete search history.

(56) References Cited

U.S. PATENT DOCUMENTS 5,274,688 A    12/1993  Grodzins ..................... 378/45
5,390,229 A     2/1995  Grodzins ..................... 378/45
5,461,654 A    10/1995  Grodzins et al. ............. 378/45
6,349,128 B1 *  2/2002  Nelson ......................... 378/44

OTHER PUBLICATIONS

Kataoka "*Standardless X-Ray Fluorescence Spectrometry*", The Rigaku Journal, vol. 6, No. 1, pp. 33-39, 1989.
D.K.G. de Boer et al., "*How Accurate is the Fundamental Parameter Approach?, XRF Analysis of Bulk and Multilayer Samples*", X-Ray Spectrometry, vol. 22, pp. 33-38, 1993.
Ida et al., "*Analysis of wrapped or cased object by a hand-held X-ray fluorescence spectrometer*", Forensic Science International, Elsevier Scientific Publishers Ireland Ltd, IE, vol. 151, No. 2-3, pp. 267-272, Jul. 16, 2005.
Cesareo et al., "*Giotto in the Chapel of the Scrovegni: EDXRF analysis of the golden haloes with portable equipment*", X-Ray Spectrometry, vol. 33, pp. 289-293, 2004.

* cited by examiner

*Primary Examiner*—Courtney Thomas
(74) *Attorney, Agent, or Firm*—Bromberg & Sunstein LLP

(57) ABSTRACT

A method and computer program software product for establishing an areal density of an elemental constituent of one layer of a stack of layers of material overlying a substrate. Incident penetrating radiation excites characteristic x-ray fluorescent radiation in multiple lines associated with each of one or more elements. Areal densities of successive layers are determined by self-consistent solution of equations relating the ratios of intensities of the characteristic fluorescence lines of successive elements.

7 Claims, 5 Drawing Sheets

```
┌─────────────────────────────────┐
│  Calibrate Instrument on        │
│  Absolute Intensities of        │
│  Characteristic Elemental Line  │
│  Pair                           │
│  Emitted by Pure Sample         │
└─────────────────────────────────┘
                 │
                 ▼
┌─────────────────────────────────┐
│  Measure Ratio of Characteristic│
│  Line Intensities in Buried     │
│  Layer of Test Sample           │
└─────────────────────────────────┘
                 │
                 ▼
┌─────────────────────────────────┐
│  Derive Areal Density of Target │
│  Element in Buried Layer        │
└─────────────────────────────────┘
```

FIG. 2

Multilayer calculation of a specific, very difficult, example for standard techniques:

Ag on SnO on Cr.2Ni.8 on SnO$_2$ on ZnO

Zinc absorbed by 1 mg/cm$^2$ of each

Areal Density assumed: 1 mg/cm$^2$
Ni = 8.9    Cr = 7.2

| | densities | 6.95 | 8.66 | 6.4 | 10.5 | | | | | |
|---|---|---|---|---|---|---|---|---|---|---|
| | | | mu values | | | | Absorption | | | |
| | | SnO$_2$ | Cr.2Ni.8 | SnO | Ag | | SnO$_2$ | Cr.2Ni.8 | SnO | Ag | Total |
| Zn 1 2 3 | 8.6 | 162 | 283 | 180 | 175 | | 3.1 | 11.3 | 3.2 | 6.3 | 690.8 |
| 4 | 9.6 | 121 | 215 | 134 | 130 | | 2.3 | 6.3 | 2.4 | 3.9 | 134.8 |
| Sn 1 2 3 | 25.3 | | 15.1 | 9.29 | 8.91 | | | 1.138 | 1.061 | 1.098 | 1.326 |
|  | 28.5 | | 10.7 | 6.68 | 41.1 | | | 1.096 | 1.044 | 1.540 | 1.761 |
| Cr 1 2 | 5.4 | | | 612 | 601 | | | | 50 | 550 | 27648 |
|  | 5.95 | | | 487 | 477 | | | | 23 | 150 | 3379 |
| Ni 1 2 | 7.5 | | | 259 | 253 | | | | 5.2 | 14.2 | 74.7 |
|  | 8.3 | | | 198 | 193 | | | | 3.6 | 7.6 | 26.9 |
| Sn 1 | 25.3 | | | | 8.91 | | | | | 1.098 | 1.098 |
|  | 28.5 | | | | 41.1 | | | | | 1.540 | 1.540 |

TABLE I

FIG. 4 overlapping lines of Ka (Z2) and Kb (Z1)

| Z1 | Z2 | Kb Z1 | Ka Z2 | Delta |
|---|---|---|---|---|
| Ti | V | 4.931 | 4.952 | 0.021 |
| V | Cr | 5.427 | 5.414 | -0.013 |
| Cr | Mn | 5.946 | 5.898 | -0.048 |
| Mn | Fe | 6.49 | 6.403 | -0.087 |
| Fe | Co | 7.057 | 6.93 | -0.127 |
| Co | Ni | 7.647 | 7.477 | -0.17 |
| Ni | Cu | 8.264 | 8.047 | -0.217 |
| Ga | As | 10.263 | 10.543 | 0.28 |
| Ge | Se | 10.981 | 11.221 | 0.24 |
| As | Br | 11.725 | 11.923 | 0.198 |
| Br | Rb | 13.29 | 13.394 | 0.104 |
| Rb | Y | 14.96 | 14.957 | -0.003 |
| Sr | Zr | 15.834 | 15.774 | -0.06 |
| Y | Nb | 16.736 | 16.614 | -0.122 |
| Zr | Mo | 15.774 | 17.478 | 1.704 |
| Mo | Ru | 19.607 | 19.278 | -0.329 |
| Ru | Pd | 21.655 | 21.75 | 0.095 |
| Pd | In | 23.816 | 24.207 | 0.391 |
| Ag | Sn | 24.942 | 25.2 | 0.258 |
| Cd | Sb | 26.093 | 26.357 | 0.264 |
| In | Te | 27.274 | 27.471 | 0.197 |
| Sn | I | 28.483 | 28.61 | 0.127 |

L Lines Au

---

Binary Coatings: Zn Ni  7.48  8.264  8.638  9.571
Sn Pb  10.5  12.6  22.2  25

Double Coatings:
Au/Ni Cu  9.711  11.459  7.477  8.264  8.047  8.904
Cr/Ni Cu
Au/Ag Ni
Sn/Cu Brass Brass is Cu (~60%, Zn(~30%) and may contain 1% Sn. measure the Sn using the L lines. Measure the Cu using the attenuation of the Zn

---

Energy Lists of Coatings to Test for Interferences

| | Au Ni Cu | Cr Ni Cu | Au Ag Ni | AuPdNiCu | AuNiCu | AuNiCuTiWP | |
|---|---|---|---|---|---|---|---|
| Cu Ka | 7.48 | 5.4 | 3 | | 7.48 | 4.5 TiKa | |
| | 8.047 | 5.9 | 7.48 | | 8.05 | 4.9 TiKb | |
| | 8.264 | 7.48 | 8.26 | | 8.26 | 7.48 NiKa | |
| | 8.8 | 8.05 | 9.71 | | 8.8 | 8.05 CuKa | |
| Ni Kb(217) | 9.71 | 8.26 | 11.44 | | 9.71 | 8.264 NiKb | |
| | 11.44 | 8.9 | 22.2 | | 11.44 | 8.396 W La | 132 eV |
| | | | 25 | | 21.75 | 9.9 Cu Kb | |
| | | | | | 22.8 | 9.67 W Lb | |
| | | | | | | 9.71 Au La | 40 eV |
| | | | | | | 11.44 Au Lb | |
| | Clean | Clean | Clean | Clean | Clean | Cu is clean | |

TABLE III

FIG. 5

ANALYSIS OF ELEMENTAL COMPOSITION AND THICKNESS IN MULTILAYERED MATERIALS The present application claims priority from U.S. Provisional Patent Application Ser. No. 60/723,384, filed Oct. 4, 2005, entitled "Multilayered Materials." The foregoing Provisional Patent Application is incorporated herein by reference.

TECHNICAL FIELD

The present invention relates to methods and devices for measuring the elemental composition and thickness of individual layers of a stack of layers overlying a substrate.

BACKGROUND ART

X-ray fluorescence (XRF) instruments measure properties of material by irradiating the material with x-rays or gamma rays and analyzing the fluorescent radiation to determine specified properties. The term "x-ray," as used herein and in any appended claims, refers broadly to penetrating radiation that is generated either by radioactive sources, or by instruments such as x-ray tubes, and encompasses within the term all forms of penetrating radiation including gamma rays. The specified properties to be determined may include the elemental composition of the irradiated object, or the distribution of a particular element in the near surface of the object, or the density of the object, or the morphology of a particular layer of material.

XRF instrumentation is the subject of U.S. Pat. Nos. 5,274,688, 5,390,229, 5,396,529, and 5,461,654, all to Grodzins, and all incorporated herein by reference. In those patents, Grodzins showed how it was possible to measure the concentration of an element in a single layer, with particular application to lead that is a constituent of a layer of lead-based paint.

As used herein and in any appended claim, the term "areal density" of an object, or of material forming a portion of an object, is defined as the thickness of the material multiplied by its density. For example, a layer of copper (density of 9 gm/cm$^3$), that is $10^{-4}$ cm thick, has an areal density of 900 µg/cm. Conversely, a determination that the thickness a copper layer with an areal density of 900 µg/cm$^2$ allows an inference that the thickness must be $10^{-4}$ cm (i.e., 1 µm).

In the prior art, where thicknesses of multilayers are to be measured using x-ray fluorescence, a beam of x-rays impinges on a multilayer sample and produces an energy versus intensity spectrum of fluorescent radiation. The energy (or, equivalently, the wavelength) of the sharp peaks in the XRF spectrum corresponds to the unique characteristic x-ray energies of the elements in the sample, while the intensity of the x-rays in the sharp peaks gives a measure of the areal density of the elements in the layers. The derived areal density, together with a known density of known material, may be used to yield the thickness of the layer, but only if the composition and ordering of overlying layers is known. (In cases where the sample is not layered but homogeneous, the intensity of the characteristic x-rays of an element gives a measure of the concentration of the element; homogeneous samples, however, are not of concern in the present invention.)

It would be valuable to establish a capability to measure the thicknesses of elements in layers that are part of a multiple layer stack of materials, in particular, layers that are buried beneath other layers, and, additionally, to be able to measure the absorption of the burying layers, as part of the same measurement.

SUMMARY OF THE INVENTION

In accordance with preferred embodiments of the invention, a method is provided for establishing an areal density of an elemental constituent of a plurality of layers of material in a multilayer structure. The method has steps of:

irradiating a first calibration sample of known elemental composition with penetrating radiation;

calibrating absolute intensities of at least a first and a second x-ray characteristic fluorescence lines emitted by the calibration sample from a single element or two elements present in at least one of the layers of the multilayer structure;

irradiating the multilayer structure with penetrating radiation;

detecting fluorescent radiation emanating from the plurality of layers;

determining a fluorescence intensity at each of the first and second characteristic fluorescence lines;

solving separately for the areal densities of the layer and absorption due to overlayers on the basis of known functional dependence of absorption at energies of the first and second characteristic fluorescence lines; and repeating the step of solving with respect to a second layer of the multilayer structure.

In accordance with alternate embodiments of the invention, the method further includes successive solution, layer by layer. The areal density of a layer may be divided by a known density of the elemental constituent in such a manner as to obtain a thickness of the layer.

In accordance with another aspect of the present invention, a computer program product is provided for use on a computer system for establishing an areal density of an elemental constituent of a layer of material among a stack comprising a plurality of layers of material. The computer program product has a computer usable medium having computer readable program code thereon, which includes program code for calibrating absolute intensities of at least a pair of x-ray characteristic fluorescence lines emitted by a calibration sample irradiated by a beam of penetrating radiation. The computer program product also has program code for solving separately for the areal densities of the layer and absorption due to overlayers on the basis of known functional dependence of absorption at energies of the first and second characteristic fluorescence lines.

BRIEF DESCRIPTION OF THE DRAWINGS

The foregoing features of the invention will be more readily understood by reference to the following detailed description, taken with reference to the accompanying drawings, in which:

FIG. 2 is a flow chart depicted the basic steps of a method in accordance with embodiments of the present invention.

DETAILED DESCRIPTION OF SPECIFIC EMBODIMENTS OF THE INVENTION

In accordance with embodiments of the present invention, both the composition and thickness of a buried layer that is part of a stack of multiple layers of materials, as well as the absorption by the layers that bury it, may be measured concurrently. In doing so, the basic ideas of the Grodzins patents referenced above, which are specifically drawn to measuring the thickness and composition of a single layer of material, are applied, by application of the invention disclosed herein, to measuring both the thickness and composition of more than one buried layer.

Figure 1:
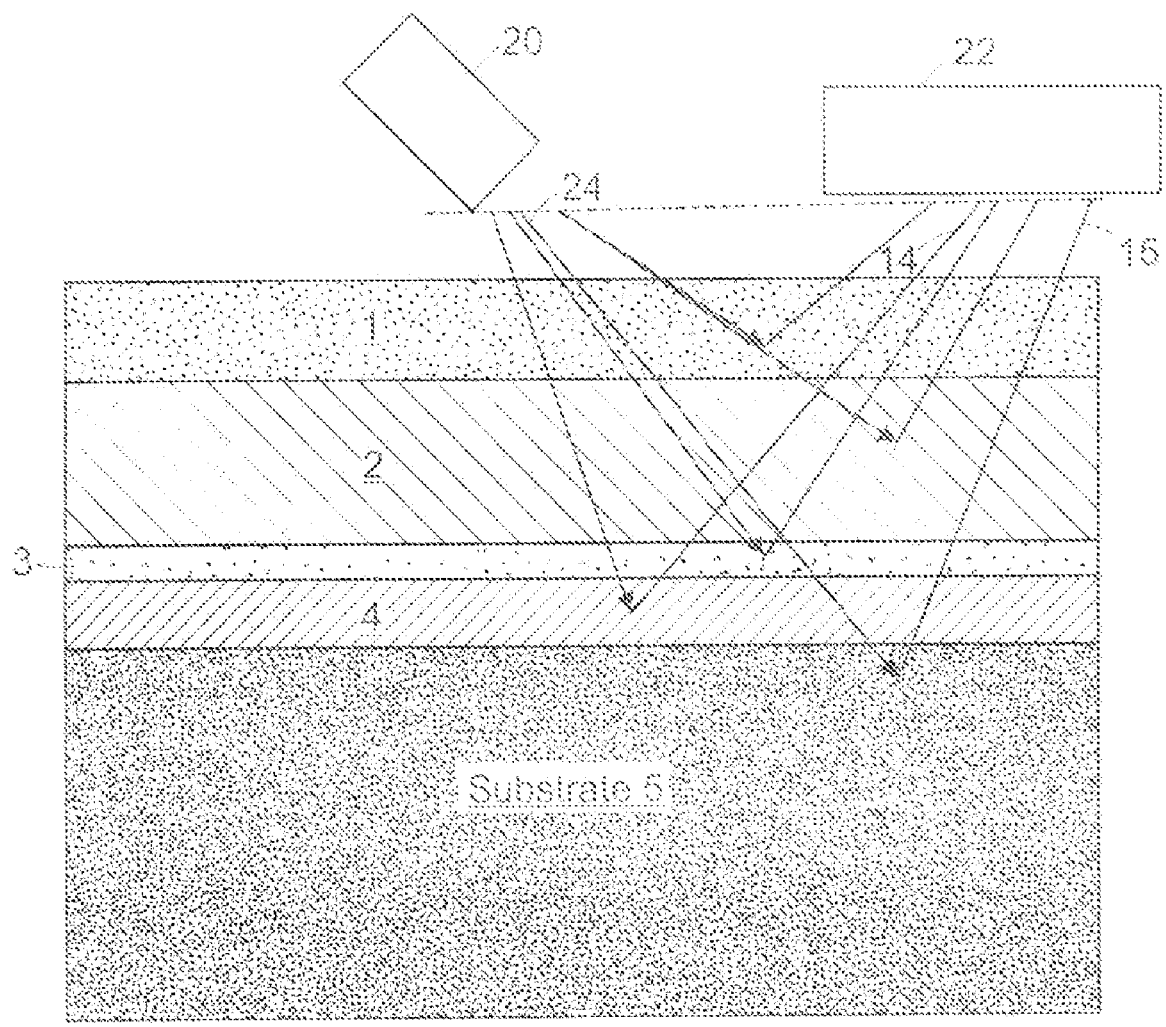
FIG. 1 depicts basic features for the discussion of XRF analysis in multilayered materials in accordance with embodiments of the present invention.

FIG. 1 depicts the situation, present in a large variety of applications, in which a substrate 5 of some material is coated with several layers 1-4 of different materials—a so-called "multilayer" structure. The layers 1-4, measured by their areal density in units of mg/cm$^2$ or g/m$^2$, have a wide range of values but are typically within an order of magnitude of 1 mg/cm$^2$ thick (10 g/m$^2$), while, in typical applications, the substrate 5 on which the layers rest is typically many times thicker than any of the layers. While there are applications with 5 or more layers, it is more typical that 2 to 3 layers on a thick substrate are the subject of measurement.

In the manufacture of multilayers, there is a need for accurate measurements of the thicknesses in order maintain the quality control of production and to certify specifications. In these quality control applications, the order of the different layers 1-4 is known. In such applications, embodiments of the present invention may be employed to make an independent measure of the areal density of one or more of the buried layers to corroborate the measure made by other means. In some applications, methods in accordance with the present invention may advantageously improve upon the accuracy of the measurement of the areal density (and hence the thickness) of the more deeply buried layers.

Moreover, certain applications call for measuring the thickness of multilayer materials in the field. In such applications it may be important to verify or determine the order of the layers by direction measurement of elemental constituents, as well as determine the thicknesses.

There may also be a need to sort mixtures of multilayered materials. In such applications it may be necessary to empirically determine the order of the multilayers.

Measurement of the Thickness of Buried Layers

Another need is that of measuring the thickness of buried layers in scrap pieces in order to determine the amount of a particular element in the scrap. The methods in accordance with the present invention may be of particular advantage in making in-the-field analyses with sufficient accuracy to be commercially useful for the reuse of scrap metals and the proper disposition of scrap waste.

XRF-based measurement of the thickness of multilayers has hitherto required a fore-knowledge of the order of the layers since the intensity spectrum of the fluoresced radiation does not have a unique solution. This is now elucidated with further reference to FIG. 1.

Source 20 of penetrating radiation 24 illuminates the sample, exciting characteristic fluorescence lines detected by detector 22. The characteristic x-rays 15 from substrate 5 are absorbed by the outer layers, independent of the order of the outer layers. Similarly, the absorption of the characteristic x-rays 14 induced in layer 4 is independent of the order of the layers 1 through 3; etc. However, layer 1, if misidentified as layer 2, would be analyzed as being thicker than it is since it would be corrected by the presumed absorption by layer 1. Layer 2 on the other hand, if misidentified as layer 1, would be analyzed as thinner than it is.

To summarize, as illustrated in the foregoing example, the standard analysis provides no unique solution to the thickness measurements if one does not know the order of the layers and the nature of the substrate.

Embodiments of the present invention, however, provide methods for determining, in a number of practical applications, the thicknesses of the layers without prior knowledge of the order of the layers.

In accordance with the present invention, the areal thickness of a buried layer can be determined from the measured relative strengths of two characteristic x-rays lines from that layer. For example, the $K_\alpha$ and $K_\beta$, or $L_\alpha$ and $L_\beta$ x-ray lines. The mathematical analysis of this fundamental idea of using relative strengths of characteristic lines is described in U.S. Pat. Nos. 5,274,688, 5,390,229, 5,396,529, and 5,461,654, all of which are incorporated by reference. As those patents show, the ratio of the intensity of two related lines from a buried layer, as compared to the ratio of the intensity of the two lines when the covering layers are removed, gives the areal density of the layer, independent of the thickness or composition of the covering layers.

More particularly, the areal density of an element Z may be given by:

$$m_Z = \left[ \frac{I_L(\beta)}{I_o \Omega_{inc} \Omega_{det} P(\beta) \epsilon(\beta)} \right]^{(R_1+R_2)/(R_1-1)} \left[ \frac{I_o \Omega_{inc} \Omega_{det} P(\alpha) \epsilon(\alpha)}{I_L(\alpha)} \right]^{(R_2+1)/(R_1-1)}$$

Here, quantities are defined as in U.S. Pat. No. 5,461,654, with $R_1$ and $R_2$, in particular, representing the ratio of the logarithms of the mass attenuation coefficients of the covering material for the incident and fluoresced radiation, respectively.

In the prior art, it was necessary to simultaneously solve a system of equations relating detected fluorescent intensities of multiple elements to areal densities of the respective elements in the various levels. This required prior knowledge of the order of the layers.

In accordance with the present teachings, however, the areal density of an element in a buried layer may be solved for, based on the recognition that the functional dependence of the differential absorption of the two characteristic lines is dominated by the $\sim E^{5/2}$ functional dependence characteristic of the photoelectric effect. Thus, when the decrement in counts, relative to an "infinitely thick" calibration sample, that is detected in the first characteristic line is compared with the decrement in counts associated with a second characteristic line, the component due to absorption in the overlayers can be separated, by standard algebraic means, from the component due to the finite thickness of the fluorescing layer.

This method can thus be widely used by XRF instruments manufactured by Thermo Electron Corp. Niton Analyzers to measure the areal density, in mg/cm$^2$, of lead in paint that has been covered by unknown thicknesses of non-lead paint of unknown composition. Lead concentrations from $\sim\mu g/cm^2$ to 10 mg/cm$^2$ can be measured by this technique.

The example of buried lead may serve to illustrate embodiments of the present invention. The absorption of x-rays in the range of interest for XRF is dominated by the photoelectric effect even in very light matrices. When the photoelectric interaction dominates, the ratio (expressed in logarithmic form) of the absorption through a layer of x-rays of two different energies, depends only on the energies of the two x-rays, and not on the areal density of the absorber or its composition. Thus, for example, a carbon layer with an areal density of 1 mg/cm² gives essentially the same ratio of absorption of the two x-rays as a copper layer of 1 mg/cm². It can then be shown that the measurement of the ratio of the intensities of the two related x-rays of lead, together with the absolute intensity of one of the lines, yields, with a calibrated instrument, the areal thickness of the element (lead, in this example) in the layer fluorescing the lines. The measurement also yields the absorption of the material overlaying the layer but does not give information as to the composition of the material that produced that absorption.

Certain conditions must be met for the successful application of the various methods of the present invention. These are now listed, with comments on how well they are met in the application of measuring the areal density of buried lead paint.

1. The fluorescence process initiated by an incident x-ray spectrum should induce characteristic fluorescent x-ray lines in fixed, known ratios.

For example: The 10.5 keV $L_\alpha$ (La) line and the 12.6 keV $L_\beta$ (Lb) lines of lead (Pb) have almost equal probability of being fluoresced.

2. The absorption of x-rays in the energy range of the fluorescent radiation should be dominated by the photoelectric effect for almost all the multi-layers.

Example: In an absorbing matrix as light as carbon, the photoelectric effect contributes 87%, of the interactions for the 12.6 keV x-ray and 93% of the interactions for the 10.5 keV x-rays.

3. The intensity of the two related x-rays from the layer being studied should be measurable through the stack of layers above. The absorption should not be so great that only the highest energy x-ray is observed, since that condition would only yield a lower limit to the areal density, of the target element.

Niton instruments are capable of quantitative analysis when the 10.5 keV La line has been absorbed by a factor of 500.

4. The target layer (i.e., the layer emitting the characteristic x-ray lines being employed) should be thinner than the saturation thickness that results from self-absorption of the characteristic x-rays in the target layer itself.

Lead thicknesses greater than about 15 mg/cm² are not quantifiable by this XRF technique using L x-rays.

5. In cases where the material composition of each of the layers is known, critical x-ray absorption edges can be accounted for. If, however, the materials in the overlayers of a target layer are not known, as is the case of measuring buried lead paint, then critical absorption must be considered. The method does not work, for example, if an upper layer has a critical absorption edge that falls between the energies of the two characteristic lines from the buried layer.

Example: The fluorescing radiation is greater than 15 keV and the only elements that satisfy the criterion (of absorbing one, but not the other, of the characteristic x-ray fluorescence lines) are germanium and arsenic, both of which have K absorption edges between 10.5 keV and 12.6 keV. So, for application of the present method, neither element can be in the overlaying paint, which is typically the case.

6. The different layers should not contain the same element to be measured; e.g. layer 1 and layer 3 should not both be layers of nickel. This is also a criterion for the standard XRF measurements which are performed on multilayers with known ordering of layers.

Example: A deeply buried lead paint cannot generally be quantified by the present methods if there is another layer of lead nearer the surface. There are special circumstances, however, in which the same element can be in two layers and measurements may still be performed in accordance with the present invention. For example, The L x-rays of a tin (Sn) layer that is near the surface may be measurable, while the L x-rays from the more deeply buried Sn cannot. In that case, the L x-rays will give the thickness of the Sn in the layer from which the L x-rays are emitted.

In accordance with preferred embodiments of the invention, determination of the areal density, and thus, for known composition, of the thickness of a buried layer with elements a, b, c and d, proceeds as follows, as described with reference to FIG. 2:

Calibration:

1. The XRF instrument is calibrated on pure samples with no overlayer by determining the XRF intensities of the sought-for characteristic lines of the pure samples of each separate element when the samples are in the target position.

2. Measurements of the absolute intensities of the characteristic lines, as above, may be repeated for each sample covered with appropriate absorbers.

a. The Grodzins patents, incorporated by reference, provide the theoretically expected changes in the intensity of the characteristic lines when the pure element samples are covered with absorbers. The calibration measurements serve to adjust the theoretical value of the exponents that appear in the equations, which are calculated using simplifying assumptions of geometries, second order effects in the fluorescence, etc.

b. The present invention advantageously applies the theoretical insight that the ratio of the absorption of the characteristic lines is, to a very good approximation, independent of the specific composition of the covering layers. This insight allows the use of a single constant in the analysis when the covering layers are of unknown composition; the constant is easily determined for each specific instrument by calibration. In the analysis of lead-based paint, the uncertainty in the measurement due to intrinsic variations of the analytic formula with atomic number is typically about 5%.

c. When all the constituents of the overlayers are known then the calibrations should be carried out using the specific constituents. This may result in reducing the uncertainties in the analysis to below the 1% level.

3. The calibrated instrument is now ready to be used in the field to determine the areal density and hence the thickness of the buried element by measuring the absolute intensities of each of the characteristic x-ray lines from the elements in each layer. The absolute intensities of two related characteristic lines, when compared to the calibration values of the absolute intensities of the two x-ray lines, obtained with no overlayer, is all that is needed to deduce the sought for areal densities. The analysis itself is given in the referenced patents.

Some examples of commercial multiple layers that may be advantageously analyzed by the method of the present invention include:

ZuNi/Fe in the Automotive Industry

Au/Ni/Cu PCB SnPb/CuPCB Ag/Ni/Cu Au/Ni/CuSn in the Electronics Industry

Cr/Ni/Cu/Al in the Metal Finishing Industry.

Figure 3:
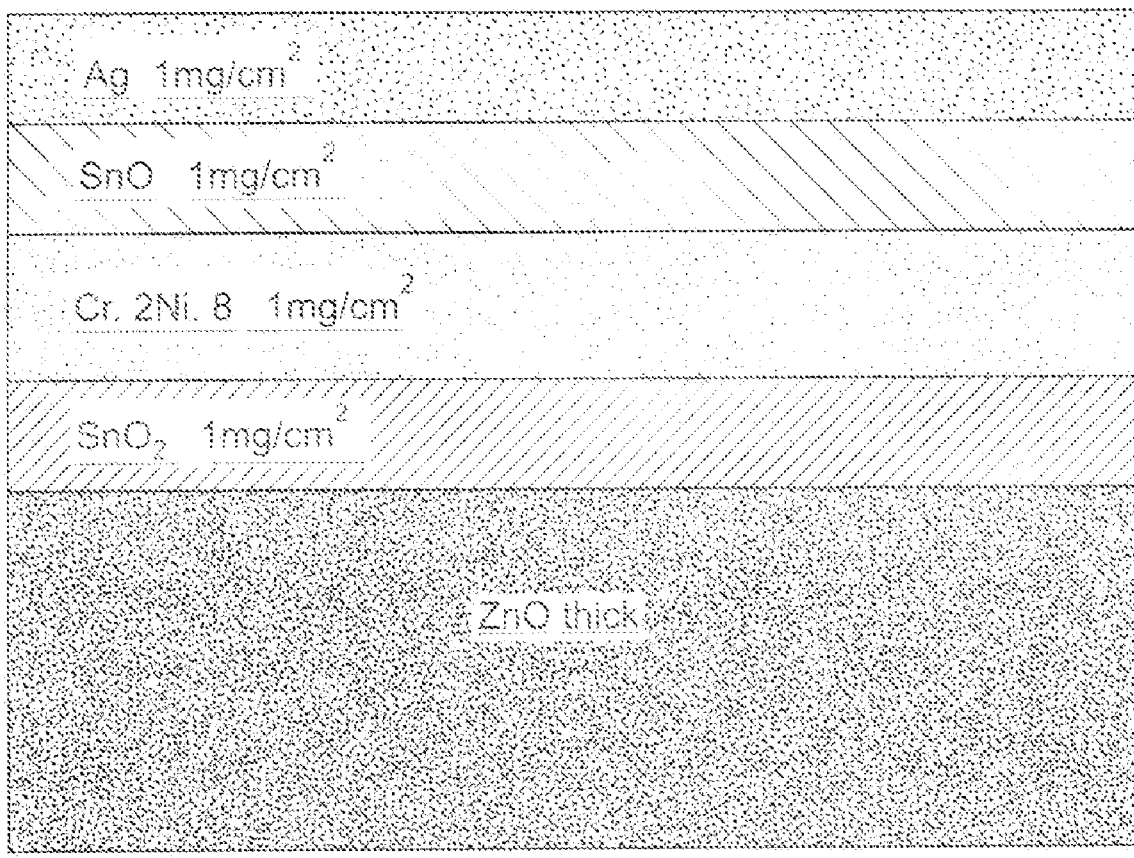
FIG. 3 is a cross-sectional representation of an exemplary multilayered material that serves as one example for the description of an embodiment of the present invention.

An example of a multilayer of commercial interest that is very difficult to do with present XRF methods is shown in FIG. 3, discussed with reference to Table I. Table I provides the attenuation of the characteristic x-rays from one deep layer due to the layers above it. Below is a set of instructions for analyzing the sample.

1. The top layer of silver can be analyzed by measuring the ratio of the intensity of the L x-rays at 2.98 keV and 3.15 keV, as taught herein. If the Ag were not the top layer, these low energy lines would not be observed. In that case one would use the Ka and Kb lines.
2. Tin is present in both layer 2 and layer 4 so that the Sn lines alone cannot yield unambiguous results. Moreover, the L lines of Sn, at 3 to 4 keV, are too heavily absorbed by the 1 mg/cm$^2$ Ag layer to be useful for measuring layer 2. The disclosed method cannot determine that layer 2 is SnO but it can determine that the measurements are consistent with a SnO layer that is 1 mg/cm2 thick. To make that determination of the SnO layer and its thickness, the disclosed method is used to measure the Ni concentration in layer 3.
3. The Nickel Ka and Kb lines at 7.47 keV and 8.26 keV are used to obtain the concentration of Ni. The concentration of chromium cannot be obtained from their K lines since, as shown in Table 1, the absorption by the upper two layers is excessive. But the concentration of Cr in layer 3 can be inferred from the concentration of Ni, if the composition of the layer is known to be Cr.2Ni.8.
4. The ratio of the intensities of the Ni Ka and Ni Kb lines gives an accurate measure of the attenuation strength of the layers above the Ni. The expected ratio of the intensity of the Kb to Ka line is 2.8. The ratio expected is the Ag layer were absent is 1.5. The ratio expected if the SnO layer were absent is 1.9. If the measured ratio of intensities is 2.8, it is an excellent check of the correctness of assumption that the order of layers is as shown in FIG. 3.
5. The analysis of the 4$^{th}$ layer also proceeds by inference. The ratio of the K lines of zinc from the ZnO substrate gives a measure of the total attenuation from all 4 layers above the substrate. The ratio of the Zn Kb intensity to the Zn Ka intensity is again used to determine that the Zn is present but too thick to quantify, and to check that there is a layer of SnO2 above. Without the SnO layer, the ratio is expected to be 3.8 while with the layer of 1 mg/cm2, the ratio drops to 3.8.

Work sheets attached as Table II list a number of elemental pairs of characteristic x-rays whose energies are close together. If both are present in the target then the lines could overlap, reducing the efficacy of the methods taught herein. In some cases the overlap in energies of the x-ray pairs is too close for separation by any current method: for example, the energies of the Kb line of Rh at 14.96 keV and the Ka line of Y, also at 14.96 keV, differ by only 3 eV. In other cases, the issue of separation is well under 100 eV so that the separation can currently be performed commercially only by wavelength dispersive techniques; examples are Cr and Mn, and Mn and Fe. In still other cases, such as Ni and Cu, the energy difference of 217 eV is attainable by state-of-the-art solid state detectors used in portable instruments.

It should be noted that, in the case of layers comprised of compounds or alloys (such as in the example of CrNi cited above), the two characteristic x-ray lines employed in accordance with the present invention may belong to different elements in the compound or alloy that make up a given layer. The two elements must be known to be in the same layer and there must be no other layer that contains the element being analyzed.

In alternative embodiments, the disclosed methods for establishing the areal density of an elemental constituent of one or more layers of a stack may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The described embodiments of the invention are intended to be merely exemplary and numerous variations and modifications will be apparent to those skilled in the art. All such variations and modifications are intended to be within the scope of the present invention as defined in the appended claims.

I claim:

1. A method for establishing an areal density of an elemental constituent of a plurality of layers of material in a multilayer structure comprising a plurality of layers of material, the method comprising:

irradiating a calibration sample of known elemental composition with penetrating radiation;

calibrating absolute intensities of at least a first and a second x-ray characteristic fluorescence lines emitted by the calibration sample from a single element or two elements present in at least a layer of the multilayer structure;

irradiating the multilayer structure with penetrating radiation;

detecting fluorescent radiation emanating from the layer;

determining a fluorescence intensity at each of the first and second characteristic fluorescence lines;

solving separately for the areal densities of the elemental constituents of the layer and absorption due to overlayers on the basis of known differential functional dependence of absorption at energies of the first and second characteristic fluorescence lines; and repeating the step of solving with respect to a second layer of the multilayer structure.

2. A method in accordance with claim 1, wherein the step of solving includes successive solution for areal density and absorption, layer by layer.

3. A method in accordance with claim 1, further including dividing the areal density of a layer by a known density of the elemental constituent in such a manner as to obtain a thickness of the layer.

4. A computer program product for use on a computer system for establishing an areal density of an elemental constituent of a plurality of layers of material among a stack comprising a plurality of layers of material, the computer program product comprising a computer usable medium having computer readable program code thereon, the computer readable program code including:

program code for calibrating absolute intensities of at least a pair of x-ray characteristic fluorescence lines emitted by a calibration sample irradiated by a beam of penetrating radiation; and program code for solving separately for the areal densities of the elemental constituents of a layer and absorption due to overlayers on the basis of known differential functional dependence of absorption at energies of the first and second characteristic fluorescence lines.

5. A method for establishing an areal density of an elemental constituent of a plurality of layers of material in an entire multilayer structure comprising a plurality of layers of material, the method comprising:

irradiating a calibration sample of known elemental composition with penetrating radiation;

calibrating absolute intensities of at least a first and a second x-ray characteristic fluorescence lines emitted by the calibration sample from a single element or two elements present in at least a layer of the multilayer structure;

irradiating the multilayer structure with penetrating radiation;

detecting fluorescent radiation emanating from the layer;

determining a fluorescence intensity at each of the first and second characteristic fluorescence lines;

solving separately for the areal density of an elemental constituent of the layer and absorption due to overlayers on the basis of known differential functional dependence of absorption at energies of the first and second characteristic fluorescence lines prior to any solution, exact or approximate, for the entire multilayer structure; and repeating the step of solving with respect to a second layer of the multilayer structure.

6. A method in accordance with claim 5, wherein the step of solving includes successive solution for areal density and absorption, layer by layer.

7. A method in accordance with claim 5, further including dividing the areal density of the layer by a known density of the elemental constituent in such a manner as to obtain a thickness of the layer.

* * * * *

UNITED STATES PATENT AND TRADEMARK OFFICE
CERTIFICATE OF CORRECTION

PATENT NO. : 7,302,034 B2 Page 1 of 1
APPLICATION NO. : 11/538652
DATED : November 27, 2007
INVENTOR(S) : Lee Grodzins It is certified that error appears in the above-identified patent and that said Letters Patent is hereby corrected as shown below:

On title page, item 73 Assignee,
replace "ThermoNITON Analyzers LLC"
with --Thermo NITON Analyzers LLC.--

Signed and Sealed this

Fifteenth Day of April, 2008

JON W. DUDAS
*Director of the United States Patent and Trademark Office*